(12) United States Patent  (10) Patent No.: US 7,883,540 B2
Niwa et al.  (45) Date of Patent: Feb. 8, 2011

(54) INTRAOCULAR LENS

(75) Inventors: Kazuharu Niwa, Nagoya (JP); Atsushi Kobayashi, Seto (JP); Kosuke Satake, Nagoya (JP)

(73) Assignee: Kowa Company, Ltd. (JP)

( * ) Notice: Subject to any disclaimer, the term of this patent is extended or adjusted under 35 U.S.C. 154(b) by 132 days.

(21) Appl. No.: 12/088,419

(22) PCT Filed: Sep. 22, 2006

(86) PCT No.: PCT/JP2006/318876

§ 371 (c)(1),
(2), (4) Date: Mar. 27, 2008

(87) PCT Pub. No.: WO2007/037180

PCT Pub. Date: Apr. 5, 2007

(65) Prior Publication Data

US 2009/0043384 A1  Feb. 12, 2009

(30) Foreign Application Priority Data

Sep. 28, 2005 (JP) ............................. 2005-282748

(51) Int. Cl.
*A61F 2/16* (2006.01)
(52) U.S. Cl. .................... 623/6.13; 623/6.37
(58) Field of Classification Search ................ 623/6.13
See application file for complete search history.

(56) References Cited

U.S. PATENT DOCUMENTS

| 5,152,788 | A | | 10/1992 | Isaacson et al. | |
| 5,213,579 | A | * | 5/1993 | Yamada et al. | 623/6.13 |
| 6,860,601 | B2 | * | 3/2005 | Shadduck | 351/176 |
| 7,122,053 | B2 | * | 10/2006 | Esch | 623/6.13 |
| 2002/0111678 | A1 | * | 8/2002 | Zadno-Azizi et al. | 623/6.34 |
| 2003/0060878 | A1 | * | 3/2003 | Shadduck | 623/6.13 |
| 2004/0082993 | A1 | * | 4/2004 | Woods | 623/6.28 |

(Continued)

FOREIGN PATENT DOCUMENTS

EP   0328117 A2   8/1989

(Continued)

OTHER PUBLICATIONS

International search report issued in corresponding application PCT/JP2006/318876, dated Oct. 17, 2006.

(Continued)

*Primary Examiner*—Corrine M McDermott
*Assistant Examiner*—Tiffany Shipmon
(74) *Attorney, Agent, or Firm*—Rossi, Kimms & McDowell LLP (57) ABSTRACT

An intraocular lens of novel structure exhibiting an excellent focus adjusting power. A hollow capsule structure is filled with a transparent liquid-like or gel-like filler (32). A front wall of the capsule structure is composed of a flexible lens front film (16), and a rear wall of the capsule structure is composed of an optical lens (18) having a diameter larger than that of the flexible lens front film (16). Under a state inserted into and attached to a capsula lentis, pressure variation of a corpus vitreum acts on the optical lens (18) to enable focal refraction power to be adjusted by utilizing swelling deformation of the lens front film (16).

25 Claims, 8 Drawing Sheets

U.S. PATENT DOCUMENTS

| | | | |
|---|---|---|---|
| 2005/0021139 A1* | 1/2005 | Shadduck | 623/6.35 |
| 2005/0125057 A1* | 6/2005 | Cumming | 623/6.37 |
| 2005/0246018 A1* | 11/2005 | Grubbs et al. | 623/6.37 |
| 2006/0122700 A1* | 6/2006 | Kurosaka et al. | 623/6.16 |
| 2006/0212116 A1* | 9/2006 | Woods | 623/6.13 |
| 2006/0271186 A1* | 11/2006 | Nishi et al. | 623/6.13 |
| 2007/0021831 A1* | 1/2007 | Clarke | 623/6.13 |

FOREIGN PATENT DOCUMENTS

| | | |
|---|---|---|
| EP | 1618857 A1 | 1/2006 |
| JP | 1-227753 A | 9/1989 |
| JP | 2-109568 A | 4/1990 |
| JP | 2-255151 A | 10/1990 |
| JP | 4-224746 A | 8/1992 |
| JP | 2001-525220 A | 12/2001 |
| JP | 2003-527898 A | 9/2003 |
| JP | 2004-528135 A | 9/2004 |
| WO | 9929266 A1 | 6/1999 |
| WO | 0166041 A1 | 9/2001 |
| WO | 03107076 A1 | 12/2003 |
| WO | 2004-072689 A2 | 8/2004 |

OTHER PUBLICATIONS

English translation of International Search Report issued in corresponding PCT/JP2006/318876, dated Sep. 18, 2008.

* cited by examiner

INTRAOCULAR LENS

This application is a U.S. National Phase Application of PCT International Application PCT/JP2006/318876 filed on Sep. 22, 2006, which is based on and claims priority from JP 2005-282748 filed on Sep. 28, 2005. The contents of these applications in their entirety are incorporated herein by reference.

TECHNICAL FIELD

The present invention pertains to an intraocular lens for insertion into the lens capsule of the eye, and relates in particular to an intraocular lens having a focus adjusting function.

BACKGROUND ART

In the past, surgical techniques for cataracts and the like have employed a procedure in which the crystalline lens inside the capsule of the eye is extracted through an incision made in the ocular tissue of the cornea (sclera) or the anterior capsule of the lens, then inserting an intraocular lens which replaces the crystalline lens through the incision, to place it within the capsule.

Intraocular lenses employed to date have been single focus lenses lacking a focus adjusting function. A resultant problem has been that while vision recovers after surgery, the ocular function lacks focus adjusting power.

Accordingly, intraocular lenses such as the following have been devised and proposed in the past as intraocular lenses having focus adjusting function.

For example, it has been proposed to use a lens having multiple focal points, such as a bifocal lens or multifocal lens, as an intraocular lens to afford simulated focus adjusting power. However, since such intraocular lenses have simultaneous vision characteristics, quality of vision tends to be poor due, for example, to diminished contrast perception, so satisfactory adjusting function has not yet been achieved.

Patent Citation 1 (JP-A-2004-528135) discloses an intraocular lens composed of a balloon made of a stretchable elastomer which is inserted into the lens capsule, and which adjusts focus through deformation conforming to movement of the capsule. However, owing to the various pressures acting within the lens capsule, it is extremely difficult in practice to precisely control deformation of the balloon placed inside it, and hence to control changes in optical characteristics based on this deformation. The resultant difficulty of ensuring basic vision and stable adjusting power makes the design impractical.

In particular, the intraocular lens taught in Patent Citation 1 promises to afford focus adjusting function through deformation of portions of weakness of the lens occurring as the lens is compressed in the diametrical direction through contraction of the ciliary muscle. However, focus adjustment through deformation of the lens is premised on normal function of the lens capsule, the zonule of Zinn, the ciliary body, and so on, and it is difficult to imagine that the ciliary muscle will be able to exert sufficient force on the inserted intraocular lens subsequent to cataract surgery. Furthermore, during distance vision, the crystalline lens assumes a flattened shape pulled by the zonule of Zinn, whereas during near vision on the other hand, the zonule of Zinn is relaxed through tensing of the ciliary muscle so that the lens recovers its original convex shape. That is, even where contraction through tensing of the ciliary muscle is assumed, it is difficult to imagine that mere relaxation of the zonule of Zinn which connects the ciliary muscle and the crystalline lens will exert compressive force on the lens sufficient to induce curving deformation of the lens as described in Patent Citation 1.

In Patent Citation 2 (JP-A-2003-527898A) it was proposed to insert an intraocular lens having an optical lens disposed in a balloon-shaped elastic member into the lens capsule, and to adjust the focal point through positioning the optical lens forward or backward by deformation of the elastic member based on movement of the lens capsule. With this intraocular lens as well, deformation of the elastic member occurs on the basis of deformation of the lens capsule, and thus as with the balloon discussed previously, there is the problem that it is difficult to control change in optical characteristics with high precision. Furthermore, slight displacement of the optical lens in the anteroposterior direction will by itself produce a change in refractive power of at most no more than about 1 D, so sufficient adjustment function cannot be achieved.

In Patent Citation 3 (JP-A-2001-525220) there was proposed an intraocular lens having a hinge portion disposed on the support member of the optical lens, and affording adjusting power through anteroposterior movement of the optical lens with respect to the optical axis using pressure change of the corpus vitreum when focusing. However, the intraocular lens disclosed in this prior art publication is similar to Patent Citation 2 discussed earlier in that the optical lens merely undergoes slight displacement in the front-back direction, so sufficient adjustment function cannot be achieved. Furthermore, after surgery the lens capsule contracts and fuses to the intraocular lens, and thus there is also a risk that movement of the optical lens will be inhibited by the lens capsule so that sufficient adjustment function is no longer achieved.

Patent Citation 1: JP-A-2004-528135
Patent Citation 2: JP-A-2003-527898
Patent Citation 3: JP-A-2001-525220

DISCLOSURE OF THE INVENTION

Problem the Invention Attempts to Solve

The present invention was made in view of the foregoing, and has as an object to provide an intraocular lens of novel structure exhibiting excellent focus adjusting power.

Means for Solving the Problem

The modes of the present invention intended to address the issues discussed above will be described hereinbelow. The constituent elements appearing in the modes herein may be combined in any number of possible combinations. The modes and technical features of the present invention are not limited by the specific disclosure herein and should be understood on the basis of the specification as a whole and the accompanying drawings, or of inventive concepts that would be apparent to the practitioner of the art from the disclosure herein.

Specifically, the present invention provides an intraocular lens for insertion into the lens capsule, having: (a) a lens front film formed of a transparent elastic film; (b) a transparent optical lens having larger diameter than the lens front film, positioned spaced apart from and in opposition to the lens front film in the direction of the optical axis; (c) a flexible annular rear film extending to the outer peripheral side of the optical lens; (d) an outer peripheral coupling portion positioned to the outer peripheral side of the lens front film and the annular rear film, and respectively supporting the outside peripheral edge of the lens front film and the outside peripheral edge of the annular rear film thereby secluding the space between the opposed faces of the lens front film and the optical lens to produce a capsule structure; (e) a transparent liquid-like or gel-like internal filler which fills the interior of the capsule structure between the opposed faces of the lens front film and the optical lens; and (f) a positioning portion extending to the outer peripheral side from the outer peripheral coupling portion and contacting the inside wall of the equatorial portion of the lens capsule thereby positioning the outer peripheral coupling portion with respect to the lens capsule.

In the intraocular lens having structure according to the present invention, the capsule structure as a whole includes the lens front film, the optical lens, the annular rear film, and the outer peripheral coupling portion; and by filling this capsule with a filler there is afforded an intraocular lens which constitutes in its entirety an integral optical component. The outer peripheral coupling portion which constitutes the outer peripheral frame of the capsule structure is then fitted within the eye, positioned with respect to the lens capsule by the positioning portion. When fitted in this state, the lens front film is subjected on either side thereof to the pressure differential between the inside and outside of the capsule, and undergoes bulging/contracting deformation on the basis of the elasticity of the lens front film per se. The optical lens is also subjected on either side thereof to the pressure differential between the inside and outside of the capsule, and undergoes displacement inside and outside the capsule on the basis of deformation of the annular rear film.

Where pressure is thereby exerted on the outside face of the optical lens, inducing the optical lens to undergo displacement inwardly into the capsule structure, pressure will in turn be exerted on the inside face of the lens front film via the filler, thereby inducing distending deformation of the lens front film by pushing it outwardly from the capsule structure. Since the lens front film is constrained with its outside peripheral edge supported by the outer peripheral coupling portion, which has higher rigidity than the lens front film, as the film undergoes distending deformation towards the outside of the lens capsule, its center section will become distended appreciably outward and deform into a dome shape. As the extent of distending deformation increases, the lens front film will assume a generally spherical shell contour with a small radius of curvature. As a result of the convex shape of the lens front film, the optical characteristics (refractive power) of the intraocular lens as a whole, whose constitution includes the lens front film, the filler, and the optical lens, will change. The focus adjusting function is afforded through this mechanism.

In the intraocular lens having structure according to the present invention, changes in refractive power occur primarily through changes induced in the curvature of the lens front film. Thus, as compared to an intraocular lens of conventional design in which changes in refractive power are produced through displacement of the lens in the anteroposterior direction, a sufficiently large range of refractive power adjustment, i.e. large change in diopter, will be possible even with small lens size. Moreover, substantially no displacement of intraocular lens per se is needed, and thus even if the lens capsule should contract and adhere to the intraocular lens, the desired refractive power adjusting function may be consistently maintained for an indefinite period. In particular, the lens front film, which directly exhibits the refractive power adjusting function through bulging deformation, is relatively small in the center of its front face, and thus adverse effects caused by contraction of the lens capsule can be advantageously avoided to a greater extent by aligning it with the location of the incision made in the lens capsule, for example.

Additionally, in the present invention in particular, the optical lens, which induces pressure deformation of the filler through a piston-like action, has a diameter dimension which is larger than the diameter dimension of the lens front film, whereby the extent of displacement of the optical lens can be amplified for transmission, with respect to the extent of displacement of the lens front film. Thus, it is possible for pressure changes in the corpus vitreum to be translated efficiently into bulging deformation of the lens front film, to achieve appreciable refractive power adjustment capability.

In the present invention, the lens front film, the optical lens, the outer peripheral coupling portion, and the filler are all transparent; however, transparence herein is not limited to colorless transparence and may include colored transparence, but it is preferable for transmittance of visible light to be at least 80% or above. On the other hand, the positioning portion may be either transparent or opaque. For example, in order to prevent unwanted reflection or refraction, an opaque member may be employed, or it may be subjected to a surface roughening process.

The specific shape of the positioning portion is not limited to any particular shape. For example, it may take the form of a simple flat circular ring which extends out about the entire circumference of the outer peripheral coupling portion, or of a number of support leg portions which project diametrical outward from the outer peripheral face of a outer peripheral coupling portion of circular ring contours; or employ any of the various other support portion structures employed in conventional intraocular lenses.

In the intraocular lens according to the present invention, in preferred practice an arrangement whereby the curvature of the outside face and the curvature of the inside face of the lens front film are different will be employed.

Furthermore, in an intraocular lens according to the present invention having such a configuration, it will be preferable for the center section of the lens front film to be thinner than its outer peripheral section.

With such a configuration it will be possible to impart a certain amount of refractive power to the lens front film per se. Moreover, by varying the thickness dimension of the lens front film, its strength and deformation rigidity can be varied as well, thus making it possible to control the mode of deformation when subjected to pressure. Specifically, change of shape of the lens front film in response to pressure changes exerted on it from the filler may be predicted using a finite element algorithm for example, and the thickness distribution of the film designed so as to give the desired lens characteristic adjusting function. Here, the lens front film may be designed so as to deform while maintaining spherical shape in order to adjust spherical face refractive power; or where for example it is desired to impart higher lens diopter adjustment power, the film may be designed to deform with an aspherical face in consideration of aberration and so on. In order to obtain such various desired lens front film shapes, it would be possible, through analysis by a finite element algorithm of the like in the design stage, to derive optimal values by varying the thickness dimension of each portion of the lens front film, for example.

In the intraocular lens according to the present invention, the connection zone between the outer peripheral coupling portion and the lens front film will preferably have a smooth face with no shoulder on the outside face.

With such a configuration it will be possible, for example, to make the entire front face of the intraocular lens (the face lying towards the cornea) a smooth face with no shoulder. It will be possible thereby to avoid adverse effects on optical characteristics caused, for example, by diffused reflection or scattering of light entering the eye through the intraocular lens, at the surface of the intraocular lens.

In the intraocular lens according to the present invention, it is preferable that with the lens inserted in the lens capsule, the optical lens undergo displacement inwardly into the capsule structure on the basis of pressure of the corpus vitreum.

With such an arrangement, pressure changes of the corpus vitreum can be utilized to adjust the refractive power of the intraocular lens. Specifically, in the case of near vision, pressure changes of the corpus vitreum produced on the basis of contraction of the ciliary muscle will cause inward displacement of the optical lens into the lens capsule. The capsule lens front film will thereby become distended and focus adjusting power will be obtained in a manner analogous to distension of the crystalline lens. Consequently, in preferred practice, with the intraocular lens inserted into the lens capsule and the ciliary muscle in the relaxed state, the optical lens will be situated sufficiently towards the outside in the capsule structure. Moreover, in preferred practice, with the intraocular lens according to the present invention inserted into the lens capsule, the optical lens will be maintained in a condition displaced further inwardly into the capsule structure, as compared with the lens by itself prior to insertion into the lens capsule. It is possible thereby to improve the stability of positioning of the optical lens.

Furthermore, in the intraocular lens of the present invention having the above configuration, it is preferable for the optical lens has a sufficient rigidity not to be deformed when subjected to pressure changes of the corpus vitreum.

With such a configuration it will be possible to bring about consistent shape change of the lens front film. Specifically, in some instances pressure changes of the corpus vitreum do not act uniformly on the optical lens; according to this configuration, the optical lens will undergo deformation while maintaining its overall shape even in such instances, thus preventing optical defects that could be caused by distortion of the optical lens.

The intraocular lens according to the present invention will preferably employ a configuration wherein the amount of inward displacement of the optical lens into the capsule structure is in a range between 0.01 mm and 1.0 mm.

While the amount of displacement of the optical lens will differ depending on the individual being fitted the intraocular lens, the diameter dimension differential between the optical lens and the lens front film, and other factors, if the amount of displacement of the optical lens is less than 0.01 mm it will be difficult to achieve the necessary level of refractive power adjusting function. On the other hand, if the amount of displacement of the optical lens exceeds 1.0 mm, there is a risk that the refractive power will change more than necessary, or that a large deformation of the lens front film or the annular rear film will result in durability problems. Accordingly, in preferred practice the amount of displacement of the optical lens produced on the basis of pressure change of the corpus vitreum will be set to an appropriate value within the range between 0.1 and 1.0 mm inclusive, as established with the lens fitted in the eye.

In preferred practice, a configuration whereby with the intraocular lens according to the present invention inserted into the lens capsule, a refractive power change of +1 D (diopter) or more will be produced by a change in curvature of the lens front film as the lens front film is pushed towards an outside of the capsule structure by a pressure change of the filler, which is in turn produced by the optical lens being pushed inwardly into the capsule structure by a change in pressure of the corpus vitreum.

In particular, it is preferable for the refractive power of the intraocular lens to vary at a minimum in a range of from +1 D to +3 D.

With this arrangement it will be possible to achieve vision in an appropriately wide range from near to far distance by fitting the intraocular lens. Refractive power here refers to the value with the lens fitted into the eye by being inserted into the lens capsule, not to that of the intraocular lens by itself measured in the outside air.

The intraocular lens according to the present invention will preferably employ a configuration wherein a refractive index differential between the lens front film and the filler is within 3%. More preferably, the refractive index differential between the lens front film and the filler will be within 1%, and especially within 0.5%.

According to this arrangement, adverse effects on the optical characteristics of the intraocular lens can be ameliorated. This is because if the refractive index differential between the lens front film and the filler is too great, appreciable reflection will occur at the interface of the lens front film with the filler, and problems such as loss of the quantity of light or glare may occur. Also, by suppressing reflection at the interface between the lens front film and the filler, it is possible to prevent refractive power from being affected by the thickness distribution of the lens front film, and to obtain consistent optical characteristics on the basis of curvature of the front face (cornea side) of the lens front film only. The optical lens will preferably be made of material with substantially the same refractive index as the lens front film, with a refractive index differential from the filler of within 3%, preferably within 1.0%, and more preferably within 0.5%.

In the intraocular lens according to the present invention, the filler will preferably have a Poisson ratio of 0.46 or above.

With such a configuration, pressure of the corpus vitreum exerted on the optical lens can effectively be transmitted to and act on the lens front film via the filler.

In the intraocular lens according to the present invention, in preferred practice at least one of the lens front film and the annular rear film will have a Young's modulus of between 0.001 MPa and 5 MPa. More preferably, the lens front film and/or the annular rear film will have a Young's modulus of between 0.01 MPa and 2 MPa.

According to this configuration, the lens front film will be able effectively change shape and recover therefrom; and displacement and recovery of the optical lens supported on the annular rear film can take place effectively. Of course, the lens front film and the annular rear film may have mutually different Young's modulus. These values can be adjusted, for example, through adjustment of the thickness of material of the lens front film and the annular rear film.

As the material for the lens front film and the annular rear film according to the present invention it would be possible to appropriately select any of various materials that are transparent and non-toxic to the body. Exemplary configurations employing appropriate materials include the following.

A configuration in which at least one of the lens front film and the annular rear film is formed of silicone rubber.

A configuration in which at least one of the lens front film and the annular rear film is formed of a hydrogel.

A configuration in which at least one of the lens front film and the annular rear film is formed of a crosslinked (meth) acrylate copolymer.

The intraocular lens according to the present invention will preferably employ a configuration in which the positioning portion and the outer peripheral coupling portion have higher rigidity than the lens front film and the annular rear film.

With such a structure, the capsule structure can be positioned stably within the capsule structure, while pressure changes of the corpus vitreum can be effectively transmitted to the capsule structure, and effectively give rise to displacement of the optical lens and deformation of the lens front film.

Moreover, the intraocular lens according to the present invention will preferably employ a structure in which the optical lens projects 0.05 mm or more towards the outside of the capsule structure from the annular rear film.

Additionally, the intraocular lens having the above structure will preferably employ a configuration in which a sharp edge is formed at a minimum about the entire circumference on the outer side of the capsule structure, in the outside peripheral edge portion of the optical lens.

With such a structure it will be possible for the outside peripheral edge portion of the optical lens on the posterior capsule side thereof to be pressed against and become wedged into the inside peripheral wall of the posterior capsule, which can effectively prevent migration of the epithelial cells of the crystalline lens. It is possible thereby to effectively prevent secondary cataracts, the most severe complication of cataract surgery. As the specific shape of the sharp edge it would be possible to appropriately employ any of the sharp edge shapes widely used in intraocular lenses in the past; the shape is not strictly speaking limited to an angled corner portion, and may be formed of several curving faces or the like.

The intraocular lens according to the present invention will preferably employ a structure furnished with refractive power adjusting means for adjusting the refractive power of the capsule structure.

As the refractive power adjusting means, there may be employed a structure whereby the refractive power adjusting means is provided by varying at least one of a refractive index and an amount of the filler.

According to this structure, it is possible to adjust refractive power for the individual user, and provide better range of vision. The refractive power adjusting means may involve varying the refractive index of the filler in the course of the intraocular lens production process; or involve varying it subsequent to manufacture, either prior to, during, or after surgery. As a specific example of such refractive power adjusting means, it would be possible to provide a sealable duct whereby the interior of the intraocular lens forming the capsule structure communicates with the space outside the intraocular lens, making it possible to inject or suction out filler through the duct.

The intraocular lens according to the present invention will preferably employ a structure wherein the refractive index of the filler is between 1.34 and 1.60.

With this structure, excellent optical characteristics may be obtained. Where the refractive index is lower than 1.34, an intraocular lens with effective refractive power and focus adjusting power will be difficult to achieve. On the other hand, where the refractive index exceeds 1.60, surface reflection becomes excessive and slight changes in shape will produce large changes in refractive power, making control difficult.

The intraocular lens according to the present invention will preferably employ a structure wherein the diameter dimension of the optical lens is between 3.0 mm and 7.0 mm.

The optical lens must be of appropriate size in order to be able to function effectively as a crystalline lens for the human eye. Additionally, since the size of the capsule of the eye with the intraocular lens inserted and accommodated therein is generally uniform, if the outside diameter dimension of the optical lens is smaller than 3.0 mm, the support portions will be too long, resulting in a tendency towards inconsistent deformation; whereas if the outside diameter dimension of the optical lens is greater than 7.0 mm, the support portions will be too short, creating a risk of insufficient cushioning action of outside force produced by deformation of the lens capsule.

Additionally, the intraocular lens according to the present invention will preferably employ a structure wherein the width dimension of the annular rear film is between 0.1 and 2.0 mm.

If the width dimension of the annular rear film is smaller than 0.1 mm it will lack sufficient flexibility, and effective displacement of the optical lens will not be produced; whereas if greater than 2.0 mm, the optical lens cannot be stably supported, creating a risk that consistent displacement of the optical lens inwardly in the lens capsule will no longer be produced.

EFFECT OF THE INVENTION

As will be apparent from the preceding description, in the intraocular lens of structure according to the present invention, pressure changes of the corpus vitreum in the eye can be utilized to efficiently bring about change in shape of the lens front film. Through changes of the curvature of the lens front film, it is possible to bring about change of the refractive power of the intraocular lens to achieve effective focus adjusting power.

EXPLANATION OF NUMERALS 10 intraocular lens
12 optical section
14 support leg portions
16 front film 18 optical lens
24 rear film
26 edge
28 outer peripheral coupling portion
30 internal space
32 filler
40 ciliary muscle
42 corpus vitreum

BEST MODE FOR CARRYING OUT THE INVENTION

In order to provide a more specific understanding of the present invention, preferred embodiments of the invention will be discussed in detail below with reference to the accompanying drawings.

Figure 1:
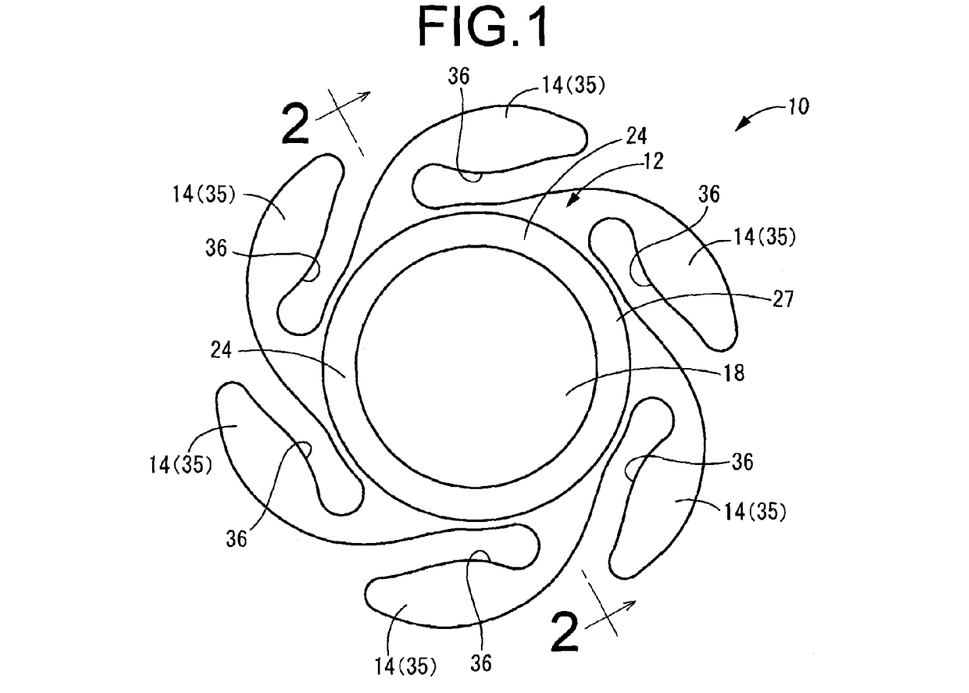
FIG. 1 is a rear view of an intraocular lens according to a first embodiment of the present invention.
Figure 2:
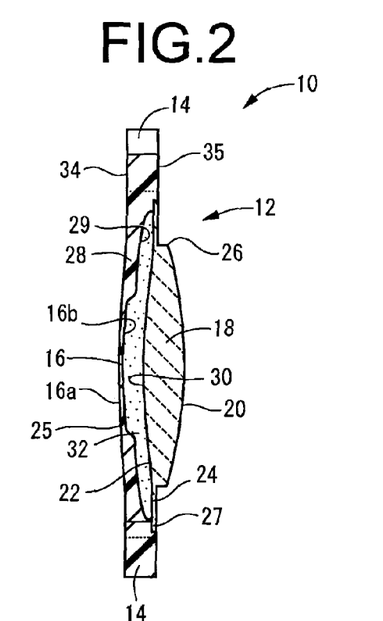
FIG. 2 is a sectional view of the intraocular lens shown in FIG. 1, taken along line 2-2.

First, FIGS. 1 and 2 depict an intraocular lens 10 as a first embodiment of the present invention. The intraocular lens 10 of this embodiment, when inserted into the lens capsule, will be positioned with the left side in FIG. 2 facing towards the cornea and with the right side facing the posterior capsule. In the description hereinbelow, "front side" will be used in reference to the left side in FIG. 2, and "rear side" will be used in reference to the right side in FIG. 2. FIG. 1 shows the back face (face lying toward the posterior capsule) of the intraocular lens 10. In FIG. 2, in order to facilitate understanding, the front film 16 and the rear film 24 are shown with exaggerated thickness dimensions.

The intraocular lens 10 has a structure in which a plurality (six in the present embodiment) of support leg portions 14 constituting the positioning portions are formed along the entire circumference of the outside peripheral section of an optical section 12 of capsule structure.

To describe in greater detail, the optical section 12 has a structure wherein an optical lens 18 and the front film 16 which constitutes the lens front film are positioned in opposition and spaced apart in the direction of the optical axis.

Figure 3:
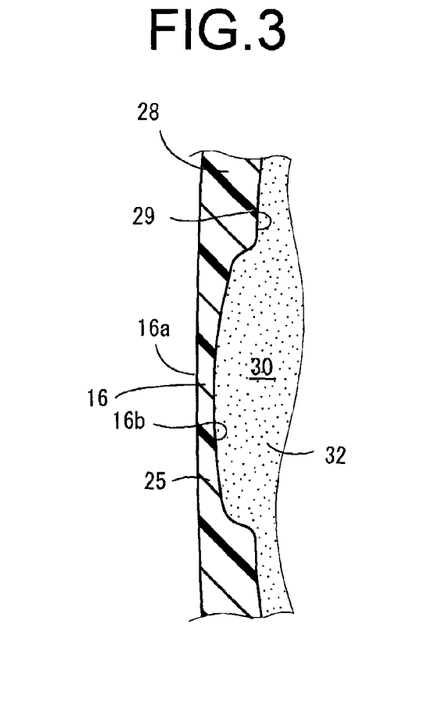
FIG. 3 is an enlarged fragmentary view of the intraocular lens shown in FIG. 1.

The front film 16 is made of transparent elastic film, and is constituted as a film of generally circular shape capable of deforming easily, and having diameter dimension smaller than the diameter dimension of the optical lens 18. In the present embodiment in particular, as shown in FIG. 3, the front film 16 is thinnest in its center section, becoming gradually thicker towards the outside peripheral edge. Specifically, the front film 16 increases in thickness in continuous stepless fashion going radially outward from its center axis, and has constant thickness along any circle centered on its center axis. The front film 16 in the present embodiment has a front face (outer face) 16a and a rear face (inner face) 16b which are spherical faces convex towards the front side. In the present embodiment, the rear face 16b has larger curvature in comparison to the front face 16a, so that the front face 16a and the rear face 16b have mutually different curvature. The curvature of the front and rear faces 16a, 16b of the front film 16 will be determined, for example, on the basis of the results of simulations carried out using a finite element algorithm during the design stage, so that they will deform to the desired curvature depending on shape change of the filler 32, discussed later.

Meanwhile, the optical lens 18 is a convex lens having outside diameter dimension greater than that of the front film 16, and whose outer face 20 and inner face 22 are each constituted by a spherical convex face which projects towards the outside of the lens. The rear film 24 constituting the flexible annular rear film is integrally formed on the optical lens 18, so as to extend diametrically outward along the entire circumference of the outside peripheral edge portion of the inner face 22. In the present embodiment in particular, the outer face 20 of the optical lens 18 projects rearward from the rear film 24; and an edge 26 of sharp edge shape is formed all the way around the circumference at the outside peripheral edge portion of the rearward-projecting outer face 20. The sharp edge shape is a cross sectional shape having an angled corner portion sufficient to provide secondary cataract inhibiting action, discussed later.

The diameter dimension of the optical lens 18 is preferably set to within a range of between 3.0 mm and 7.0 mm. The optical lens 18 must be of appropriate size in order to be able to function effectively as a crystalline lens for the human eye. Additionally, since the size of the capsule of the eye with the intraocular lens 10 inserted and accommodated therein is generally uniform, if the outside diameter dimension of the optical lens 18 is smaller than 3.0 mm, the support leg portions 14 will be too long, resulting in a tendency towards inconsistent deformation; whereas if the outside diameter dimension of the optical lens 18 is greater than 7.0 mm, the support leg portions 14 will be too short, creating a risk of insufficient cushioning action of outside force, discussed later.

The extent of projection of the outer face 20 from the rear film 24 will preferably bet 0.05 mm or more. If the extent of projection is less than 0.05 mm, it will be difficult to achieve sufficient force of contact against the inside wall of the posterior capsule, discussed later. As the specific shape of the sharp edge formed at the edge 26 it would be possible to appropriately employ any of the sharp edge shapes widely used in intraocular lenses in the past; the shape is not strictly speaking limited to an angled corner portion and may be formed of several curving faces, due to considerations such as convenience in processing.

The width dimension of the rear film 24 in the direction of lens diameter is preferably between 0.1 and 2.0 mm. If the width dimension of the rear film 24 is smaller than 0.1 mm it will lack sufficient flexibility, and effective displacement of the optical lens 18 will not be produced. On the other hand, if greater than 2.0 mm, it will be difficult to stably support the optical lens 18, creating a risk that consistent displacement of the optical lens 18 will no longer be produced.

The materials for forming the front film 16 and the optical lens 18 may be selected appropriately from among any of various materials, provided that they have sufficient transmittance of visible light to serve as an intraocular lens and are non-toxic to the body; example of favorable ones are polydimethyl siloxane, polydimethyl diphenyl siloxane, and other silicone rubbers; hydroxyethyl methacrylate and other hydrogels; or crosslinked (meth)acrylate copolymers. Monomers including one or more of the (meth)acrylic acid esters listed in (i) below are preferred. Optional monomers such as those listed in (ii) below may be included appropriately. Optionally, additives such as those listed in (iii) below may be added if needed.

(i) Included Monomers

Linear, branched, or cyclic alkyl (meth)acrylates such as the following:

Methyl (meth)acrylate, ethyl (meth)acrylate, butyl (meth)acrylate, cyclohexyl (meth)acrylate, etc.

Hydroxyl group-containing (meth)acrylates such as the following:

Hydroxyethyl (meth)acrylate, hydroxybutyl (meth)acrylate, diethylene glycol mono(meth)acrylate, etc.

Aromatic ring-containing (meth)acrylates such as the following:

Phenoxyethyl (meth)acrylate, phenyl (meth)acrylate, phenyl ethyl (meth)acrylate, etc.

Silicone-containing (meth)acrylates such as the following:
Trimethyl siloxy dimethylsilylmethyl (meth)acrylate, trimethyl siloxy dimethylsilylpropyl (meth)acrylate, etc.

Herein, the expression "(meth)acrylates" is used to refer collectively to "acrylates" and "methacrylates"; this convention will also be employed for other (meth)acrylic derivatives to be discussed later.

(ii) Optional Monomers (Meth)acrylamide and derivatives thereof such as the following:
(Meth)acrylamide, N,N-dimethyl (meth)acrylamide, etc.
N-vinyl lactams such as the following:
N-vinyl pyrrolidone, etc.
Styrene or derivatives
Crosslinking monomers such as the following:
Butanediol di(meth)acrylate, ethylene glycol di(meth)acrylate (iii) Additives Thermal polymerization initiators, photopolymerization initiators, photosensitizers, etc.
Dyes etc.
UV absorbers etc.

While it is preferable for the front film 16 and the optical lens 18 to be formed of identical material in order to prevent unanticipated refraction or diffuse reflection between the component, and to facilitate bonding them together; however, it is possible for them to be made of mutually different materials.

During the process of integrally molding the front film 16 and the optical lens 18 using monomer materials such as the above, it is possible to use any of the various methods known in the conventional art. For example, the desired front film 16 or optical lens 18 could be obtained by a forming process involving cutting, or by a forming process involving molding. Where a cutting process is employed, prescribed polymer components selected from monomer materials such as the above will be subjected to polymerization to form an appropriate blank such as a rod, block, or slab; and the blank will then undergo a cutting process using a lathe or the like to produce the front film 16 or optical lens 18 of the desired shape. Where a molding process is employed, using a mold cavity that corresponds in shape to the intended shape of the front film 16 or optical lens 18, prescribed polymer components selected from monomer materials such as the above will be introduced into the mold cavity and subjected in situ to an appropriate polymerization procedure to obtain the front film 16 or optical lens 18 of the desired shape. The method of polymerization of the monomer material will be selected appropriately according to the particular monomer material, from among the various known methods such as thermal polymerization, photopolymerization, or some combination of these.

In the intraocular lens 10 of the present embodiment, the front film 16 and the rear film 24 will preferably each have Young's modulus of between 0.001 MPa and 5 MPa, more preferably between 0.01 MPa and 2 MPa. With this arrangement, shape deformation and recovery of the front film 16, as well as displacement and recovery of the optical lens 18, can take place effectively as will be discussed later. The elasticity of the front film 16 and the rear film 24 will be adjusted, for example, by adjusting the thickness of these components. The values may be same the same between the front film 16 and the rear film 24, or different.

The optical lens 18 will be formed with consideration to a thickness dimension sufficient to impart rigidity such that it will not deform when subjected to pressure changes of the corpus vitreum, so that pressure changes of the corpus vitreum will be exerted uniformly on the filler 32, discussed later, and bring about consistent deformation of the front film 16.

The front film 16 and the optical lens 18 having the structure described above are juxtaposed in the direction of the optical axis, with the outer peripheral edge portion 27 of the rear film 24 juxtaposed against the rear end face of the outer peripheral edge portion of the outer peripheral coupling portion 28 which has been integrally formed with the peripheral edge portion 25 of the front film 16, and fastened together through adhesion, welding, or the like. The outer peripheral edge portion of the front film 16 is thereby supported directly by the outer peripheral coupling portion 28, and the outer peripheral edge portion of the optical lens 18 is supported by the outer peripheral coupling portion 28 via the rear film 24. The intraocular lens 10 will thereby be imparted with a capsule structure having an internal space 30 situated between the opposed faces of the front film 16 and the optical lens 18 and isolated from the outside. In the present embodiment, the thickness dimension of the outer peripheral coupling portion 28 becomes gradually smaller going towards the center, and an inner recess face 29 is formed on the inner face of the outer peripheral coupling portion 28, forming the internal space 30 inclusive of this inner recess face 29. The rear end face of the outer peripheral edge portion of the outer peripheral coupling portion 28 is formed depressed by a depth dimension equal to the thickness dimension of the rear film 24, so that no step is formed between the peripheral edge portion 27 of the rear film 24 and the rear face 35 of the support leg portions 14.

In this way, the optical lens 18 is coupled to the outer peripheral coupling portion 28 via the readily deformable rear film 24, making its position in the direction of the optical axis displaceable with respect to the front film 16. The amount of inward displacement of the optical lens 18 into the optical section 12 will preferably be set to within a range of between 0.01 mm and 1.00 mm, when inserted into the lens capsule.

Also, in the present embodiment, the outer peripheral coupling portion 28 and the front film 16 are integrally formed. Here, the thickness dimension of the outer peripheral coupling portion 28 on the inner recess face 29 side decreases gradually going towards the center. The connecting portion of the front film 16 with the outer peripheral coupling portion 28 at the front face is a stepless flat surface. Diffuse reflection occurring on the surface of the intraocular lens 10 is avoided thereby.

The filler 32 constituting the internal filler fills the entirety of the internal space 30 which has been formed between the opposed faces of the front film 16 and the optical lens 18. This filler 32 is clear liquid or gel-like member with a Poisson ratio of 0.46 or above, which readily undergoes change in shape in response to displacement of the optical lens 18.

Here, the refractive index of the filler 32 is higher than the refractive index of the aqueous humor, preferably between 1.34 and 1.60. If the refractive index is lower than 1.34, effective lens power and focus adjusting power will not be obtained, whereas if the refractive index exceeds 1.60, surface reflection will become excessive.

If the refractive index is too high, refractive power will change appreciably with a slight change in shape of the optical section 12, making it difficult to control refractive power when inserted into the eye (when unadjusted). For example, where the filler 32 has refractive power of 1.4, refractive power of close to +3 D can be obtained by pushing of the optical lens 18 by 0.02 mm through a change in pressure of the corpus vitreum. This is far greater than the change in refractive power afforded by structures proposed in the past, in which the optical lens simply moves forward and backward.

In preferred practice the refractive power differential between the filler 32 and the front film 16 will be 3.0% or less, more preferably 1.0% or less, and especially 0.5% or less. If the refractive power differential between the filler 32 and the front film 16 is too large, there will be appreciable reflection at the interface of the front film 16 and the filler 32, and problems such as loss of the quantity of light or glare may occur. Also, as will be discussed later, in order to bring about ready deformation of the front film 16 through shape changes of the filler 32 it is preferable for the dimension of the front film 16 to be smaller, but if the dimension of the front film 16 is smaller, a resultant problem will be a smaller effective optical section. Accordingly, the refractive index of the front film 16 and the filler 32 are made substantially the same, in order to achieve optical characteristics which are unaffected by the thickness distribution of the front film 16 and which are dependent exclusively upon the curvature of the front face 16a of the front film 16.

The filler 32 is not limited to any particular material provided it has the characteristics mentioned above. A liquid, crosslinked gel, or the like may be employed. Exemplary liquids are aqueous solutions of inorganic salts such as sodium chloride or calcium chloride, of sugars such as dextran, glucose, or hydropropylethyl cellulose, or of organic synthetic polymers such as polyethylene glycol, polyvinyl pyrrolidone, or polyacrylic acid. Examples of gels are silicone based gels such as those disclosed in JP 2-109568A; photopolymerizable gels such as those disclosed in JP 2-255151A, or gels obtained through crosslinking of the above organic synthetic polymer aqueous solutions with gamma rays, an electron beam, or other form of radiation.

When filling the internal space 30 with the filler 32, it is possible, for example during the intraocular lens 10 manufacturing stage, to fill a recess formed in advance on the inside face of the front film 16 with the filler 32, and to then juxtapose the optical lens 18 thereon like a lid; or to immerse the front film 16 and the optical lens 18 in the filler 32 and juxtapose them while immersed in the filler 32.

Figure 4:
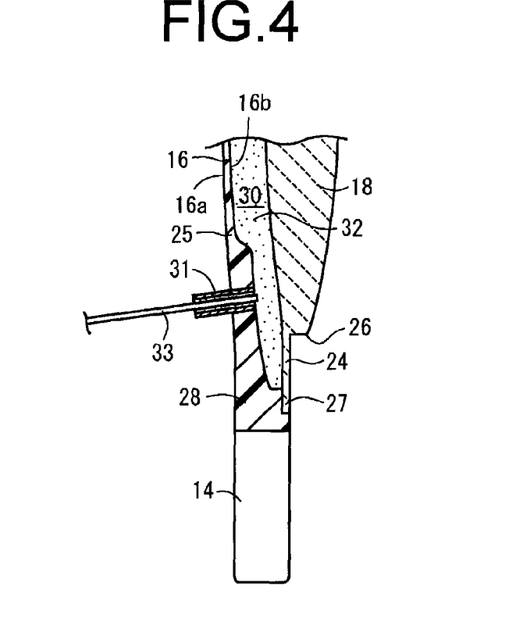
FIG. 4 is an illustration depicting refractive power adjusting means of the present invention.

It would also be possible to carry out filling with the filler 32 after the intraocular lens 10 has been manufactured, for example, after it has been inserted into the eye. Specifically, this could be accomplished as depicted in FIG. 4 for example, by providing a duct 31 through which the internal space 30 communicates with the outside of the intraocular lens 10, making it possible to insert a filler injection tube 33 for injecting the filler 32 in through this duct 31 as taught in JP-A-1-227753 or JP-A-4-224746. Once the filler injection tube 33 has been withdrawn, leaking out of the filler 32 through the duct 31 can be prevented, for example, by filling the inside of the duct 31 with a sealing gel as taught in JP-A-4-224746; or by sealing the distal end of the duct 31 with adhesive or by welding. More preferably, the duct 31 will be formed so as to pass through the outer peripheral coupling portion 28, to avoid adverse effects on the optical characteristics of the intraocular lens 10. Also, in preferred practice the duct 31 will be disposed so as to project towards the front face side, and will project towards the outside of the eye with the intraocular lens 10 fitted into the capsule. With this arrangement, with the lens fitted into the capsule either during or after surgery it will be easy to inject or drain the filler 32 through the duct 31. The refractive index of the optical section 12 can be adjusted by adjusting the amount of the filler 32, and the refractive power adjusting means can be advantageously constituted using the duct 31.

The optical section 12 having the structure described above is provided at its outside peripheral edge portion with a plurality (six in the present embodiment) of support leg portions 14. The plurality of support leg portions 14 are identical in shape, and are formed so as to extend diametrically outward towards the outer peripheral side from the outer peripheral edge portion of the optical section 12. In the present embodiment in particular, front faces 34 situated on the cornea side of the support leg portions 14 and rear faces 35 situated on the posterior capsule side thereof are flat surfaces and are integrally formed with the outer peripheral coupling portion 28 by virtue of unchanging width dimension approximately identical to that of the outer peripheral edge portion of the outer peripheral coupling portion 28. It will be apparent therefrom that the thickness dimension of the support leg portions 14 is greater than that of the front film 16 and the rear film 24. The rigidity of the support leg portions 14 is higher than the rigidity of the front film 16 and the rear film 24.

A notch 36 is formed in each support leg portion 14, and by means of this notch 36 the support leg portion 14 is formed with an arcuate bowed inner face so as to jut out in the circumferential direction from the outside peripheral side towards the inside peripheral side. In the present embodiment in particular, the notch 36 is formed as a bowed face which is concave towards the outside in the diametrical direction of the intraocular lens 10, with the generally medial section thereof in the direction of projection from the optical section 12 being constricted in width, and with the distal end section of generally elliptical shape spreading out slightly in the circumferential direction of the optical section 12.

With consideration to the outside diameter dimension of the optical section the outside diameter dimension of the plurality of bowed support leg portions 14 have an (i.e. diameter dimension of circumscribed circle around the plurality of support leg portions 14) has been set appropriately for the size of the typical capsule of the human eye. With this arrangement, the outside peripheral edge portions of the support leg portions 14 will be disposed in contact against the inside wall of the equatorial portion of the capsule, whereby the outer peripheral coupling portion 28, and hence the optical section 12, can be positioned advantageously within the capsule.

The intraocular lens 10 having the structure described above will be fitted in the eye in the usual known manner by making an incision in part of the capsule of the eye, and after removing the crystalline lens by suction or the like, inserting the folded or unfolded intraocular lens through the incision wound. This operation can be carried out advantageously using an appropriate insertion instrument if needed.

Figure 5:
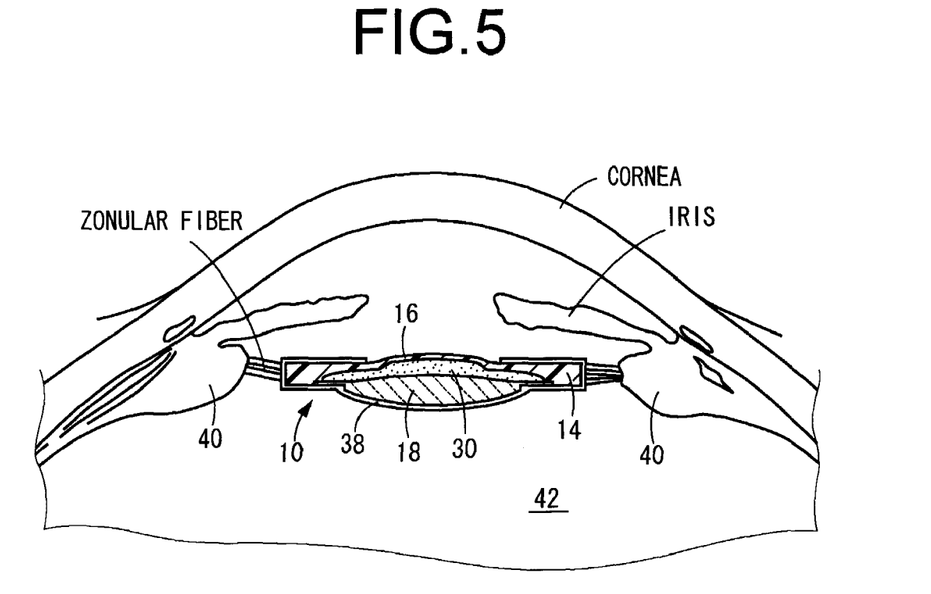
FIG. 5 is a longitudinal sectional view of the intraocular lens shown in FIG. 1 shown an implanted state.

As depicted in FIG. 5, when implanted so as to be accommodated entirely within the interior of the capsule 38, the intraocular lens 10 will be positioned within the capsule 38 by the outside peripheral edge portions of the support leg portions 14 pushing against the inside wall of the equatorial portion of the capsule 38, due to the resilience of the support leg portions 14. If needed, the position of the intraocular lens 10 within the capsule 38 can be adjusted using an appropriate instrument, thereby positioning the intraocular lens 10 within the capsule 38 so that the optical axis of the optical section 12 is generally aligned with the center axis of the ophthalmic axis.

Figure 6:
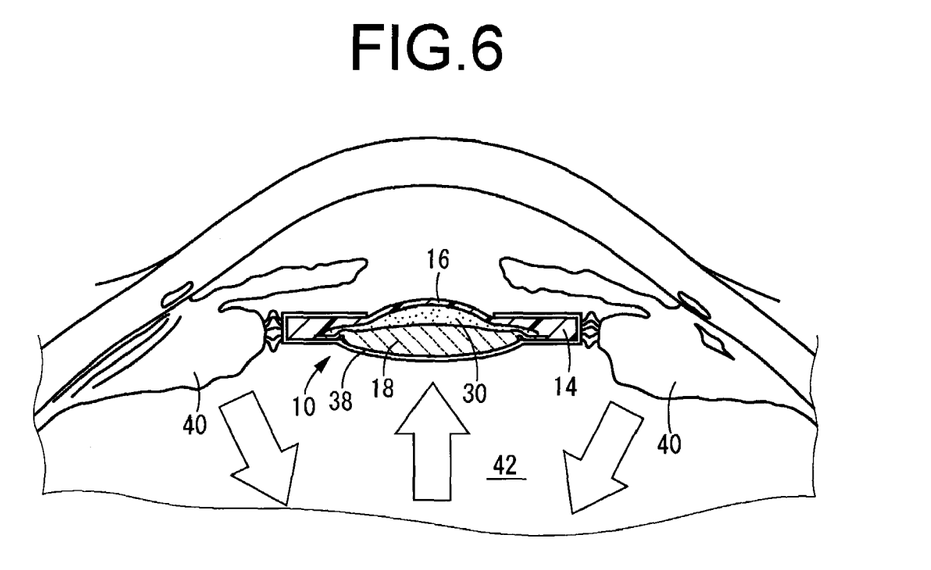
FIG. 6 is a longitudinal sectional view of the intraocular lens shown in FIG. 5, depicted under by pressure exerted by the corpus vitreum.

As shown in FIG. 6, with the intraocular lens 10 inserted into the capsule 38, during near vision, pressure changes of the corpus vitreum 42 produced by tension of the ciliary muscle 40 will create force acting to push the optical lens 18 in the forward direction (towards the cornea). The optical lens 18 will then undergo displacement inwardly into the optical section 12, causing the lens front film 16 to become distended the forward direction (towards the cornea through pressure changes in the filler 32.

In the present embodiment, the front film 16 will thereby become projected forward with a convex spherical face, increasing its curvature and thereby raising the refractive power of the front film 16 further in the positive direction. The location of the focal point can then be brought closer to the forward direction (towards the cornea), affording focus adjustment function during near vision. In preferred practice the intraocular lens 10 will be designed so as to give rise refractive power change of +1 D while inserted into the lens capsule; preferably, the refractive power will be set so as to vary within a range of at least between +1 D and +3 D.

By changing the refractive power of the intraocular lens 10 of the present embodiment through change in the curvature of the front film 16 in this way, greater change in refractive power can be achieved in comparison to a structure in which lens position is displaced in the anteroposterior direction. Since such large changes can be obtained with only slight changes in the extent of projection of the front film 16, even if the capsule 38 should contract and fuse to the intraocular lens 10 for example, there will be no risk that deformation of the front film 16 will be hindered thereby, and it will be possible to achieve consistent refractive power adjusting function for an indefinite period.

The optical lens 18 in the present embodiment is formed with sufficient rigidity that it will not deform in shape when subjected to pressure changes of the corpus vitreum 42. Thus, even if pressure changes do not act uniformly on part of the optical lens 18, the optical lens 18 will maintain its shape while undergoing displacement, making it possible to consistently and efficiently increase the refractive power of the front film 16.

Additionally, in the intraocular lens 10 of the present embodiment, the rigidity of the support leg portions 14 is higher than the rigidity of the front film 16 and the rear film 24. Thus, pressure changes of the corpus vitreum 42 can be ameliorated through absorption by deformation of the support leg portions 14, and pressure changes of the corpus vitreum 42 can be effectively exerted on the optical section 12.

While the intraocular lens 10 illustrated in FIGS. 1 through 6 has been described in detail by way of a first embodiment of the present invention, the invention should not be construed as limited to the specific description of the intraocular lens 10 hereinabove. In order to provide a better understanding of the present invention, several additional specific embodiments of the invention will be given by way of example hereinbelow, together with additional drawings. Components and regions which are similar in structure to the intraocular lens 10 of the preceding first embodiment are assigned identical symbols in the drawings, and are not discussed in any detail.

Figure 7:
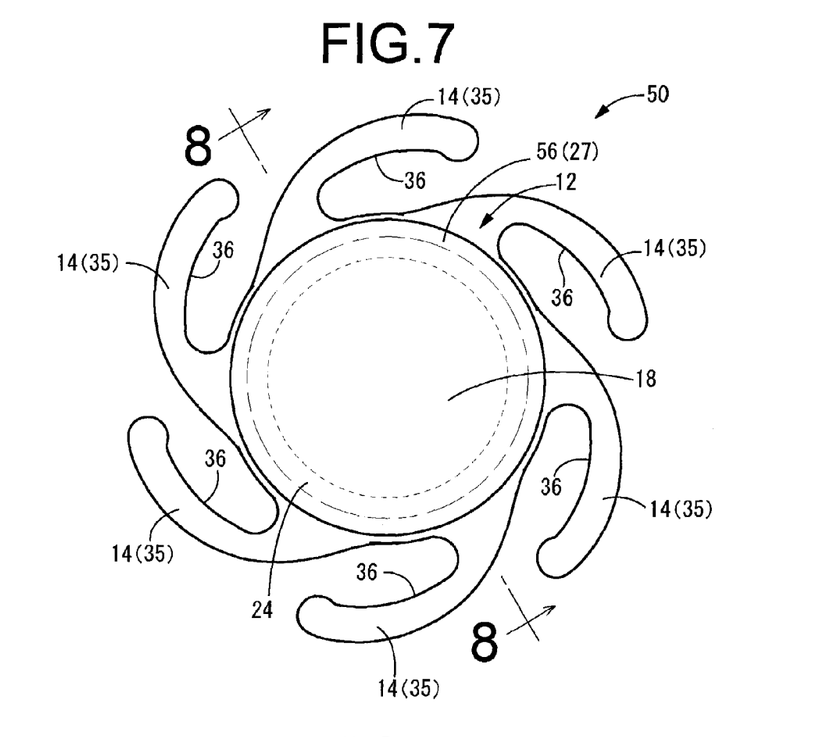
FIG. 7 is a rear view of an intraocular lens according to a second embodiment of the present invention.
Figure 8:
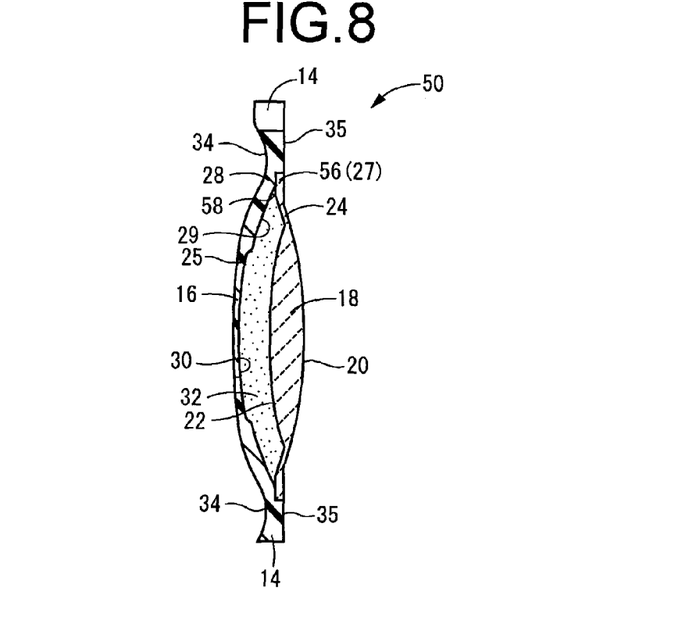
FIG. 8 is a sectional view of the intraocular lens shown in FIG. 7, taken along line 8-8.

FIGS. 7 and 8 depict an intraocular lens 50 as a second embodiment of the present invention. In the present embodiment, the shape of the notch 36 in the support leg portions 14 is formed with an arcuate bowed inner face, so that each support leg portion 14 juts out from the same side in the circumferential direction about the center axis of the optical section 12. In the present embodiment in particular, the notch 36 is formed as a bowed face which is convex towards the outside in the diametrical direction of the intraocular lens 50, whereby the generally medial section of the support leg portion 14 in the direction of projection from the optical section 12 is constricted in width and the distal end section is narrower in width than the support leg portions in the preceding first embodiment. Also, the projecting distal end portion of the support leg portion 14 has a rounded shape projecting slightly inward in the diametrical direction. Furthermore, while the rear face 35 situated on the posterior capsule side of the support leg portion 14 is a flat surface similar to the preceding first embodiment, the front face 34 situated on the cornea side is a bowed face of gradually increasing thickness dimension towards the distal end from the basal end portion of the support leg portion 14. It is possible thereby to achieve more effective cushioning action through absorption of deformation of the lens capsule.

The outer face 20 of the optical lens 18 in the present embodiment is not projected out rearward from the rear film 24, and the connecting section of the rear film 24 with the outer face 20 is a generally flat surface. That is, the outer face 20 of the optical lens 18 in the present embodiment lacks an edge 26 having a sharp edge shape like that in the preceding first embodiment.

With the intraocular lens 50 in the present embodiment in the unadjusted state not subjected to the action of pressure of the corpus vitreum, the optical lens 18 will project out slightly to the rear. The rear film 24 in the region thereof between the optical lens 18 and the outer peripheral edge portion 27 affixed to the outer peripheral coupling portion 28 will thereby be inflected slightly towards the rear, with the outer peripheral edge portion 27 constituting a mounting edge portion 56 for anchoring to the outer peripheral coupling portion 28. In the present embodiment, only the diametric outside section of the outer peripheral edge portion 27 is juxtaposed against the inner recess face 29 of the outer peripheral coupling portion 28. The diametric inside section of the outer peripheral edge portion 27 projects inwardly into the internal space 30. The internal space 30 is thereby given a shape having a shoulder portion 58 which is formed by the diametric inside section of the outer peripheral edge portion 27.

Figure 9:
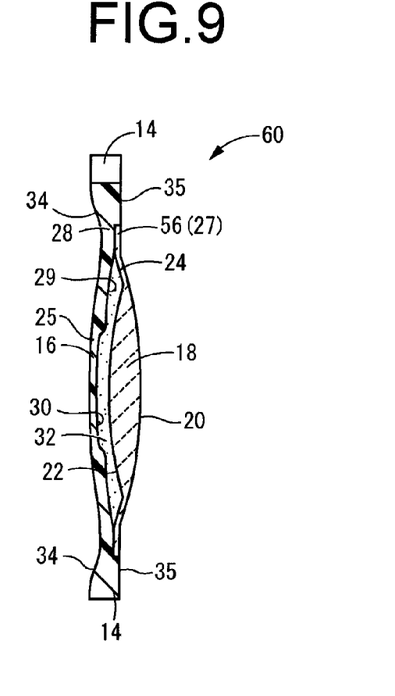
FIG. 9 is a sectional view of an intraocular lens according to a third embodiment of the present invention.

Next, an intraocular lens 60 is shown in FIG. 9 by way of a third embodiment of the present invention. In the intraocular lens 60 of the present embodiment and the intraocular lens 70 according to a fourth embodiment described below, the rear face shape is substantially identical to that of the intraocular lens 50 of the second embodiment shown in FIG. 7 and thus will not be illustrated or discussed here.

The intraocular lens 60 in the present embodiment is generally similar in shape of the intraocular lens 50 of the second embodiment described above, but has smaller thickness dimension in the anteroposterior direction due to the smaller volume of the internal space 30 in comparison with the intraocular lens 50. Since substantially the entire mounting edge portion 56 of the rear film 24 of the intraocular lens 60 is juxtaposed against the inner recess face 29, the internal space 30 of the present embodiment has a shape lacking a shoulder portion 58 in the intraocular lens 50 discussed earlier.

Figure 10:
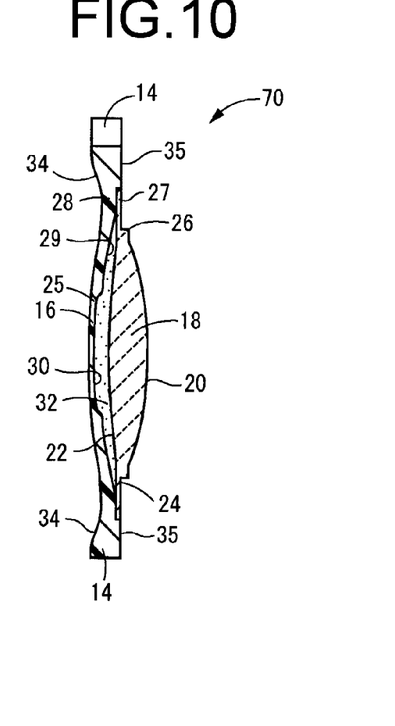
FIG. 10 is a sectional view of an intraocular lens according to a fourth embodiment of the present invention.

While the outer face 20 of the optical lens 18 in the intraocular lenses 50, 60 of the second and third embodiments above have flat shape lacking a sharp edge shape, it is of course possible for the outer face 20 of this optical lens 18 to be furnished with a sharp edge shape similar to that of the first embodiment described previously. An intraocular lens 70 having such a sharp edge face is shown in FIG. 10 by way of a fourth embodiment.

Specifically, the intraocular lens 70 of the fourth embodiment is equivalent to providing the intraocular lens 60 of the preceding third embodiment with an optical lens 18 of shape generally similar to the preceding first embodiment.

Figure 11:
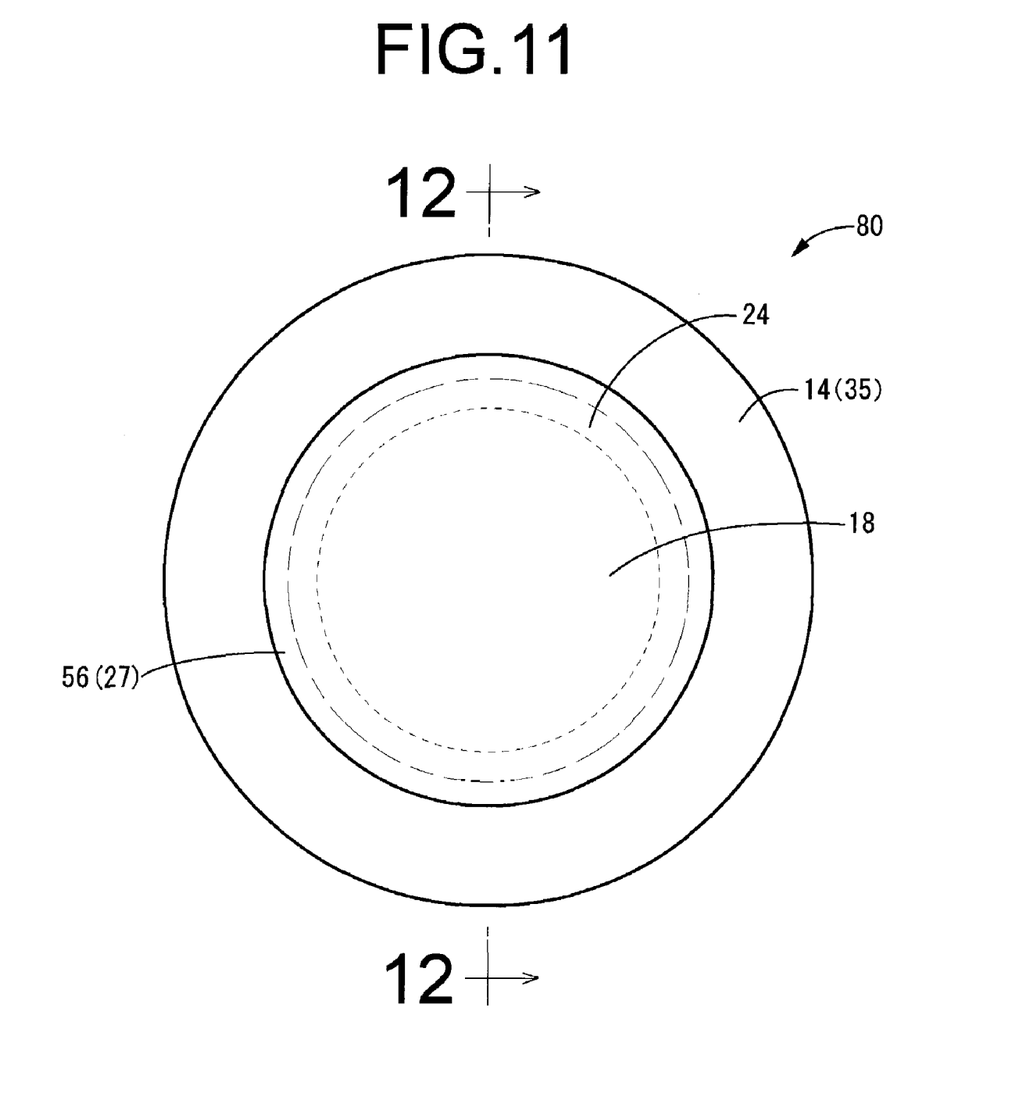
FIG. 11 is a sectional view of an intraocular lens according to a fifth embodiment of the present invention.
Figure 12:
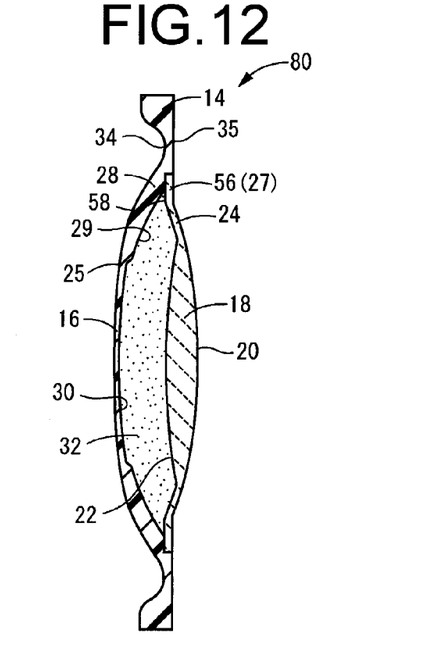
FIG. 12 is a sectional view of the intraocular lens shown in FIG. 11, taken along line 12-12.

Next, an intraocular lens 80 is shown in FIGS. 11 and 12 by way of a fifth embodiment of the present invention. In the intraocular lens 80, the support leg portion 14 has generally circular ring contours extending diametrically outward all the way around the circumference of the optical section 12. With this arrangement, the optical section 12 can be positioned in a stable manner within the lens capsule. In the support leg portion 14 of the present embodiment as well, the front face 34 on the cornea side has gradually increasing thickness dimension moving diametrically outward. As in the intraocular lens 50 of the previous second embodiment, in the internal space 30 in the present embodiment the diametrical inside section of the mounting edge portion 56 of the rear film 24 projects inwardly into the internal space 30, giving it a shape having a shoulder portion 58.

Figure 13:
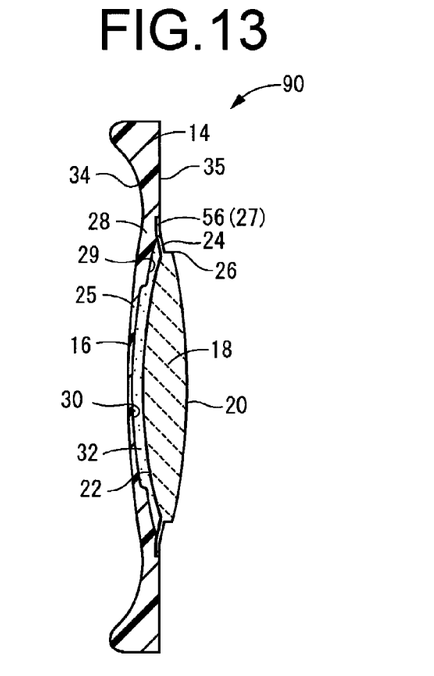
FIG. 13 is a sectional view of an intraocular lens according to a sixth embodiment of the present invention.

Next, FIG. 13 shows an intraocular lens 90 by way of a sixth embodiment of the present invention. In the intraocular lens 90 of the present embodiment, the rear face shape is substantially identical to that of the intraocular lens 80 of the fifth embodiment shown in FIG. 11 and thus will not be illustrated or discussed here.

The intraocular lens 90 of the sixth embodiment is equivalent to reducing the volume of the internal space 30 of the intraocular lens 80 of the preceding fifth embodiment, as well as providing it as the optical lens 18 with an optical lens 18 furnished with an edge 26 having sharp edge shape similar to that of the intraocular lens 10 in the preceding first embodiment. Also, in the intraocular lens 90 of the present embodiment, the outer peripheral edge portion of the front face 34 of the support leg portion 14 is a convex spherical face projecting in the forward direction along the entire circumference.

While the present invention has been shown hereinabove through certain preferred embodiments, these are merely exemplary and the present invention should in no way be construed as limited by the specific disclosures of the embodiments.

For example, the lens front film, the optical lens, the outer peripheral coupling portion, and the internal filler in the preceding embodiments are not limited to being transparent and colorless, and may instead be transparent and colored. In preferred practice the lens front film, the optical lens, the outer peripheral coupling portion, and the internal filler will have visible light transmittance of at least 80%. The positioning portion may be transparent or opaque.

Figure 14:
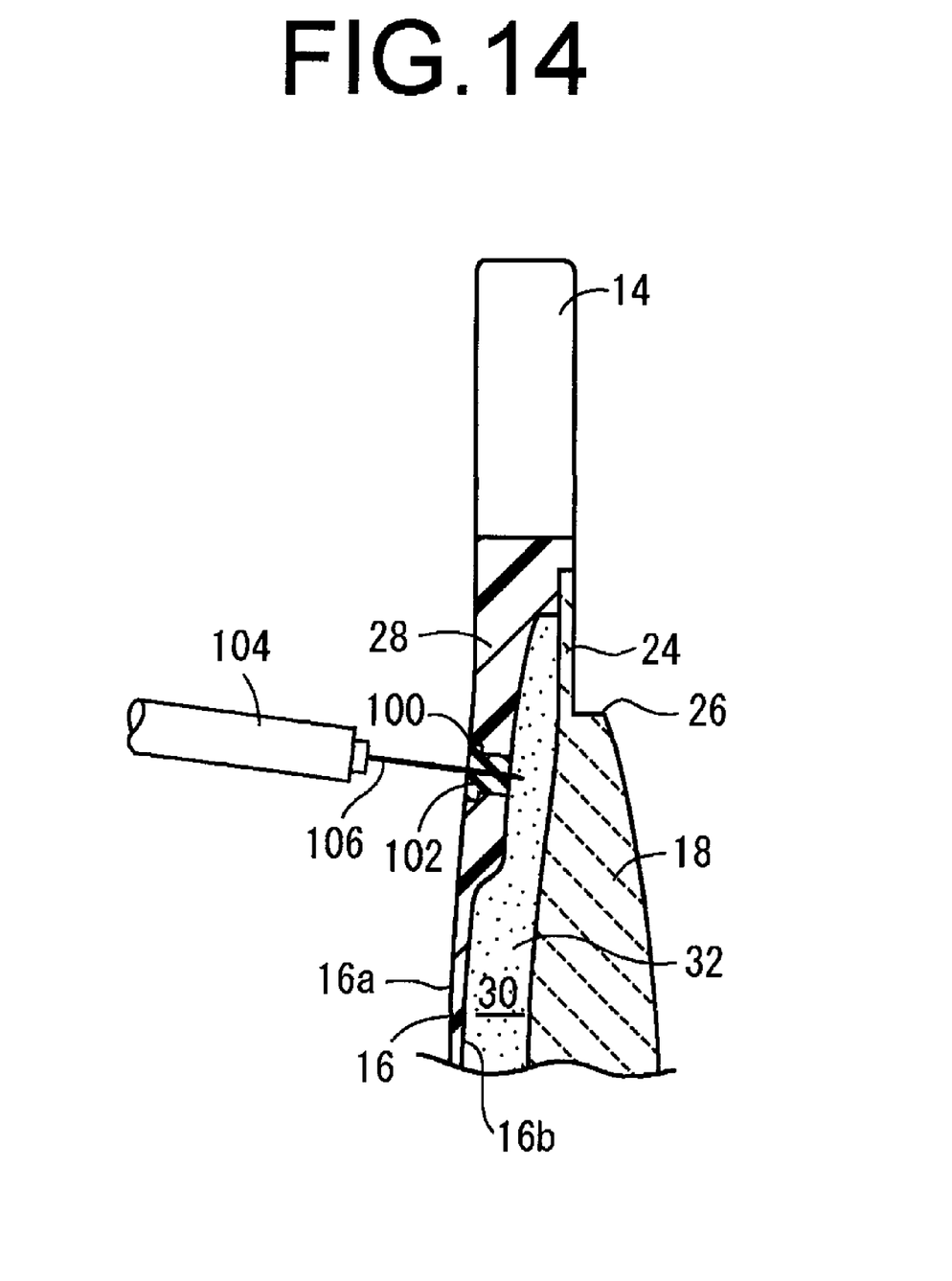
FIG. 14 is an illustration of an intraocular lens according to the present invention furnished with a different form of refractive power adjusting means.

In the preceding embodiments, changing of the refractive power through differing levels of internal filler was described by way of example as the refractive power adjusting means for adjusting the refractive power of the intraocular lens. However, it would also be acceptable for example to vary refractive power by supplementation with an internal filler having a different refractive index, or replacement with an internal filler having a different refractive index, via the aforementioned duct 31. Furthermore, rather than providing a duct 31 it would be acceptable, as shown for example in FIG. 14, to form a small hole 100 passing through the outer peripheral coupling portion 28, and to fit an elastic seal 102 composed of highly elastic rubber material or the like into this small hole 100, thereby allowing the filler 32 to be injected or drained by piercing the elastic seal 102 with an injection needle 106 using a syringe 104. The elastic recovery force of the elastic seal 102 can be utilized to seal off the small-diameter hole made by the injection needle 106 after the injection needle 106 has been withdrawn.

As yet a different embodiment, it would be possible to embed tiny receptacles known as microcapsules between the opposed faces of the lens front film and the optical lens, and to then induce rupture of the microcapsules using a laser or the like, in order to change the refractive power of the intraocular lens. For example, it would be possible to adjust the refractive power of the intraocular lens by altering the deformation characteristics of the front film by bringing about a substantial change in volume of the internal space by inducing rupture of microcapsules. By bringing about a substantial change in the amount of filler by inducing rupture of microcapsules which contain as a core substance filler identical to the internal filler; or by altering the refractive index of the internal filler by inducing rupture of microcapsules which contain as a core substance an internal filler with a different refractive index, causing the filler with the different refractive index to become admixed with the internal filler. Furthermore, deformation characteristics may be altered through substantial modification of the dimensions of the front film by restraining it with an annular member. According to these embodiments, the refractive power of the intraocular lens can be adjusted without the need to make holes or the like connecting the internal space of the intraocular lens to the outside space.

Moreover, while the intraocular lenses in the preceding embodiments all have convex lens contours with spherical convex front and back faces, lens shape is not limited to convex lens shapes; for example, concave lens shapes would be acceptable, as would tabular shapes having prescribed thickness dimension.

Furthermore, the components of the front film, the outer peripheral coupling portion, and the positioning portion need not be integrally formed, and may be constituted as mutually separate elements. For example, the positioning portion could be constituted as a separate element from the front film and the outer peripheral coupling portion, and the capsule structure and the positioning portion constituted as separate elements for insertion into the lens capsule separately, with the intraocular lens of the present invention being assembled within the capsule. With this arrangement, the intraocular lens of the present invention can be inserted through a smaller incision, thereby facilitating the insertion procedure, as well as reducing the burden on the user.

While not given individually herein, the present invention may be reduced to practice in various other modes incorporating variations, modifications and improvements which would be apparent to those skilled in the art, and these embodiments will of course fall within the scope of the invention insofar as they do not depart from the spirit thereof.

The invention claimed is:

1. An intraocular lens for insertion into a lens capsule, comprising:
    a lens front film having a diameter and formed of a transparent elastic film;
    a transparent optical lens having a larger diameter than the diameter of the lens front film, positioned spaced apart from and in opposition to the lens front film in a direction of an optical axis;
    a flexible annular rear film extending to an outer peripheral side of the optical lens;
    an outer peripheral coupling portion positioned to an outer peripheral side of the lens front film and the annular rear film, and supporting an outside peripheral edge of the lens front film and an outside peripheral edge of the annular rear film respectively thereby secluding a space between opposed faces of the lens front film and the optical lens to produce a capsule structure;
    a transparent liquid or gel internal filler which fills an interior of the capsule structure between the opposed faces of the lens front film and the optical lens; and
    a positioning portion extending to an outer peripheral side from the outer peripheral coupling portion and contacting an inside wall of an equatorial portion of the lens capsule thereby positioning the outer peripheral coupling portion with respect to the lens capsule.

2. The intraocular lens according to claim 1, wherein a curvature of an outside face and a curvature of an inside face of the lens front film are different.

3. The intraocular lens according to claim 2, wherein a center section of the lens front film is thinner than an outer peripheral section.

4. The intraocular lens according to claim 1, wherein a connection zone between the outer peripheral coupling portion and the lens front film have a smooth face with no shoulder on an outside face.

5. The intraocular lens according to claim 1, wherein with the lens inserted in the lens capsule, the optical lens undergoes displacement inwardly into the capsule structure on the basis of pressure of a corpus vitreum.

6. The intraocular lens according to claim 5, wherein the optical lens has a sufficient rigidity not to be deformed when subjected to pressure changes of the corpus vitreum.

7. The intraocular lens according to claim 1, wherein an amount of inward displacement of the optical lens into the capsule structure is in a range between 0.01 mm and 1.0 mm.

8. The intraocular lens according to claim 1, wherein with the intraocular lens inserted into the lens capsule, a refractive power change of +1 D or more is produced by a change in curvature of the lens front film as the lens front film is pushed towards an outside of the capsule structure by a pressure change of the filler, which is in turn produced by the optical lens being pushed inwardly into the capsule structure by a change in pressure of the corpus vitreum.

9. The intraocular lens according to claim 8, wherein the refractive power of the intraocular lens varies at a minimum in a range of from +1 D to +3 D.

10. The intraocular lens according to claim 1, wherein a refractive index differential between the lens front film and the filler is within 3%.

11. The intraocular lens according to claim 1, wherein the filler have a Poisson ratio of 0.46 or above.

12. The intraocular lens according to claim 1, wherein at least one of the lens front film and the annular rear film has a Young's modulus of between 0.001 MPa and 5 MPa.

13. The intraocular lens according to claim 1, wherein at least one of the lens front film and the annular rear film is formed of silicone rubber.

14. The intraocular lens according to claim 1, wherein at least one of the lens front film and the annular rear film is formed of a hydrogel.

15. The intraocular lens according to claim 1, wherein at least one of the lens front film and the annular rear film is formed of a crosslinked (meth)acrylate copolymer.

16. The intraocular lens according to claim 1, wherein the positioning portion and the outer peripheral coupling portion have higher rigidity than the lens front film and the annular rear film.

17. The intraocular lens according to claim 1, wherein the optical lens projects 0.05 mm or more towards the outside of the capsule structure from the annular rear film.

18. The intraocular lens according to claim 1, wherein a sharp edge is formed at a minimum about an entire circumference on an outer side of the capsule structure, in an outside peripheral edge portion of the optical lens.

19. The intraocular lens according to claim 1, further comprising refractive power adjusting means for adjusting the refractive power of the capsule structure.

20. The intraocular lens according to claim 19, wherein the refractive power adjusting means is provided by varying at least one of a refractive index and an amount of the filler.

21. The intraocular lens according to claim 1, wherein the refractive index of the filler is between 1.34 and 1.60.

22. The intraocular lens according to claim 1, wherein a diameter dimension of the optical lens is between 3.0 mm and 7.0 mm.

23. The intraocular lens according to claim 1, wherein a width dimension of the annular rear film is between 0.1 and 2.0 mm.

24. The intraocular lens according to claim 1, wherein the outer peripheral side of the lens front film is constrained by the outer peripheral coupling portion, which has higher rigidity than the lens front film.

25. The intraocular lens according to claim 1, wherein the rear film is readily deformable, and wherein the optical lens is coupled to the outer peripheral coupling portion via the readily deformable rear film so that the optical lens undergoes displacement in the direction of the optical axis with respect to the lens front film due to deformation of the readily deformable rear film.

* * * * *